(12) United States Patent
Gojon-Romanillos

(10) Patent No.: US 8,389,005 B2
(45) Date of Patent: Mar. 5, 2013

(54) SYSTEMIC TREATMENT OF PATHOLOGICAL CONDITIONS RESULTING FROM OXIDATIVE STRESS AND/OR REDOX IMBALANCE

(75) Inventor: Gabriel Gojon-Romanillos, San Pedro Garza Garcia (MX)

(73) Assignee: Nuevas Alternativas Naturales Thermafat, S.A.P.I. de C.V., Monterrey, N.L. (MX)

( * ) Notice: Subject to any disclaimer, the term of this patent is extended or adjusted under 35 U.S.C. 154(b) by 245 days.

(21) Appl. No.: 12/405,165

(22) Filed: Mar. 16, 2009

(65) Prior Publication Data

US 2009/0181081 A1 Jul. 16, 2009

Related U.S. Application Data

(62) Division of application No. 10/463,765, filed on Jun. 18, 2003, now abandoned.

(60) Provisional application No. 60/389,491, filed on Jun. 19, 2002.

(51) Int. Cl.
*A61K 9/00* (2006.01)
*A61K 33/00* (2006.01)
*A01N 59/00* (2006.01)

(52) U.S. Cl. ........ 424/463; 424/400; 424/600; 424/703; 424/711

(58) Field of Classification Search .................. 424/400, 424/600, 703, 711
See application file for complete search history.

(56) References Cited

U.S. PATENT DOCUMENTS

| | | | |
|---|---|---|---|
| 2,897,121 A | | 7/1959 | Wagner |
| 4,031,267 A | | 6/1977 | Berry et al. |
| 4,481,195 A | | 11/1984 | Rubin |
| 4,555,522 A | * | 11/1985 | Martin ............................ 514/449 |
| 4,900,538 A | * | 2/1990 | Suwa et al. ...................... 514/34 |
| 6,242,491 B1 | * | 6/2001 | Kaddurah-Daouk ......... 514/565 |
| 7,022,315 B2 | * | 4/2006 | Neuwelt et al. ................. 424/59 |
| 2001/0001664 A1 | | 5/2001 | Sherwood et al. |
| 2002/0077316 A1 | * | 6/2002 | Dasseux et al. |

FOREIGN PATENT DOCUMENTS

| | | | |
|---|---|---|---|
| WO | WO 99/55344 | * | 11/1999 |
| WO | WO 01/80832 | * | 11/2001 |

OTHER PUBLICATIONS

Laishley et al., Canadian Journal of Microbiology, vol. 17, 1971, p. 889-895.*
Hildebrandt et al., FEBS Journal, 275, 2008, p. 3352-3361.*
Blachier et al., Amino Acids, 2010, 39:335-347.*
Chemical Abstract 103:49472q. Protection against toxic redox cycles between benzo[a]pyrene-3,6-quinone and its quinol by 3-methylcholanthrene-inducible formation of the quinol mono- and diglucuronide.
Chemical Abstract 104:83518q. In vivo effects of NAC on GSH metabolism and on the biotransformation of carcinogenic and/or mutagenic compounds.
Chemical Abstract 109:49848r. Peroxide damage to the eye lens in vitro prevention by pyruvate.
Chemical Abstract 117:124292a. HIV-induced cysteine deficiency and T-cell dysfunction. A rationale for treatment with NAC.
Chemical Abstract 118:36647k. Exhaustive physical exercise causes oxidation of GSH status in blood: prevention by antioxidant administration.
Chemical Abstract 120:94995z Chemoprevention of colon cancer by thiol and other organosulfur compounds.
Chemical Abstract 121:52138n. Quinone methide mediates in vitro induction of ODC by the tumor promoter BHT hydroperoxide.
Chemical Abstract 122:53893n. Nitric oxide produced by human B-lymphocytes inhibits apoptosis and Epstein-Barr virus reactivation.
Chemical Abstract 122:312365d. Endogenous intracellular glutathionyl radicals are generated in neuroblastoma cells under hydrogen peroxide oxidative stress.
Chemical Abstract 125:158088u. In vitro comparative assessment of the antioxidant activity of nacystelyn against three reactive oxygen species.
Chemical Abstract 125:299270j. Pyrrolidine dithiocarbamate inhibits the production of IL-6, IL-8, and granulocyte-macrophage colony-stimulating factor.
Chemical Abstract 125:321400a. Metal catalyzed inactivation of bovine glucose-6-phosphate dehydrogenase-role of thiols.
Chemical Abstract 126:29487v. Fibronectin-fragment mediated cartilage chondrolysis II. Reparative effects of antioxidants.
Chemical Abstract 126:29488w. Fibronectin-fragment mediated cartilage chondrolysis I. Suppression by antioxidants.
Chemical Abstract 127:93549q. Intracellular thiol redox status affects rat cytomegalovirus infection of vascular cells.
Chemical Abstract 127:203894h. Synergistic induction of DNA strand breakage caused by NO together with catecholamine. Implications for neurodegenerative disease.
Chemical Abstract 127:230414h. Hydrogen peroxide-induced expression of the proto-oncogenes c-jun, c-fos, and c-myc, in rabbit lens epithelial cells.
Chemical Abstract 127:230417m. Thiols and disulfides can aggravate PN-dependent inactivation of a-antiproteinase.
Chemical Abstract 127:243220s. Selective inhibition of IkBa phosphorylation and HIV-1 LTR-directed gene expression by novel antioxidant compounds.
Chemical Abstract 127:260773s. The effect of NO release rates on the oxidation of human low-density lipoprotein.
Chemical Abstract 128:47708p. Nutritional aspects of dissimilatory sulfate reduction in the human large intestine.
Chemical Abstract 128:98808d. Spatial distribution of GSH, GSH-related, and antioxidant enzymes in cultured mouse embryos.

(Continued)

*Primary Examiner* — Ruth A Davis
(74) *Attorney, Agent, or Firm* — Clark & Elbing LLP

(57) ABSTRACT

Alterations of redox homeostasis in mammals underlie a host of symptoms, syndromes and diseases, including AIDS and cancer, which can be successfully treated by administration to a mammal of therapeutically-effective amounts of sulfide compounds and/or thiosulfate compounds and/or thionite compounds and/or thionate compounds and/or any organic, inorganic or organometallic precursors thereof. The unique compositions of this invention contain one or more "active sulfur compounds" in combination with each other or with other therapeutic agents. The invention also encompasses the varying modes of administration of the therapeutic compounds.

24 Claims, No Drawings

OTHER PUBLICATIONS

Chemical Abstract 128:165547h. Reactive oxygen species are involved in shear stress-induced intercellular adhesion molecule-1 expression in endothelial cells.
Chemical Abstract 128:293361e. Glucose deprivation-induced cytotoxicity and alterations in mitogen-activated protein kinase activation are mediated by oxidative stress in multidrug-resistant human breast carcinoma cells.
Chemical Abstract 128:320423k. Activation of transcriptionally active nuclear factor-kB by tumor necrosis factor-a and its inhibition by antioxidants in rat thyroid FRTL-5 cells.
Chemical Abstract 129:8993a. Antioxidants reduce cyclooxygenase-2 expression, prostaglandin production, and proliferation in colorectal cancer.
Chemical Abstract 129:79579j. Mammalian thioredoxin is a direct inhibitor of apoptosis signal-regulating kinase (ASK)-1.
Chemical Abstract 129:90474s. Tripyruvin (glycerol tripyruvate) for delivery of therapeutically effective amounts of pyruvate.
Chemical Abstract 129:147521m. The redox state as a correlate of senescence and wasting and as a target for therapeutic intervention.
Chemical Abstract 129:239856c. Improvement by several antioxidants of macrophage function in vitro.
Chemical Abstract 130:21523r. Nitric oxide donor-induced hyperpermeability of cultured intestinal epithelial monolayers: role of superoxide radical, hydroxyl radical, and PN.
Chemical Abstract 130:164182q. PN causes proton leak in brain mitochondria.
Chemical Abstract 130:164708r. Reducing compounds initiate the TRP2-catalyzed conversion of L-dopachrome to DHICA.
Chemical Abstract 130:193466r. Inactivation of heart dihydrolipoamide dehydrogenase by peroxidase-dependent oxidant systems.
Chemical Abstract 130:217636z. The role of oxidative imbalance in progression to AIDS: effect of the thiol supplier NAC.
Chemical Abstract 130:250581a. Study on the apoptosis in PC12 cell induced by dopamine.
Chemical Abstract 131:57301b. In vivo modulation of rodent GSH and its role in PN-induced neocortical synaptosomal membrane protein damage.
Chemical Abstract 131:69583h. Regulation of cytochrome P-4501A metabolism by GSH.
Chemical Abstract 131:97553s. The biological significance of non-enzymic reaction of menadione with plasma thiols: enhancement of menadione-induced cytotoxicity to platelets by the presence of blood plasma.
Chemical Abstract 131:97567z. Attenuation of galactose-induced cataract by pyruvate.
Chemical Abstract 131:100702x. Decreased intracellular superoxide levels activate sindbis virus-induced apoptosis.
Chemical Abstract 131:156034y. Basal protein phosphorylation is decreased and phosphatase activity increased by an antioxidant and a free radical trap in primary rat glia.
Chemical Abstract 131:156247v. Cysteine and GSH in catabolic conditions and immunological dysfunction.
Chemical Abstract 131:195634p. NAC protects epithelial cells against the oxidative imbalance due to clostridium difficile toxins.
Chemical Abstract 131:242377u. Vitamin C: poison, prophylactic or panacea.
Chemical Abstract 131:281112y. NAC, a cancer chemopreventive agent, causes oxidative damage to cellular and isolated DNA.
Chemical Abstract 131:282518x. Reactivity of biologically important thiol compounds with superoxide and hydrogen peroxide.
Chemical Abstract 131:282520s. Peroxidase/hydrogen peroxide enhances hypersensitivity responses induced by eugenol: inhibitory effect of an antioxidant, lipoic acid.
Chemical Abstract 131:297044p. Ceruloplasmin has a distinct active site for catalyzing glutathione-dependent reduction of alkyl hydroperoxides.
Chemical Abstract 131:317411m. Prevention of quinone-mediated DNA arylation by antioxidants.
Chemical Abstract 131:318712x. Role of transcription factor NF-kB in asbestos-induced TNF-a response from macrophages.
Chemical Abstract 131:331954x. Supplementation of NAC inhibits NF-kB activation and protects against alloxan-induced diabetes in CD-1 mice.
Chemical Abstract 131:335657a. Eosinophil apoptosis is mediated by stimulators of cellular oxidative metabolism and inhibited by antioxidants: involvement of a thiol-sensitive redox regulation in eosinophil cell death.
Chemical Abstract 132:21721v. Antioxidant properties of pyruvate mediate its potentiation of beta-adrenergic inotropism in stunned myocardium.
Chemical Abstract 132:59115p. Antioxidant properties of albumin: effect on oxidative metabolism of human neutrophil granulocytes.
Chemical Abstract 132:76521k. Potential role of cerebral GSH in the maintenance of blood-brain barrier integrity in rat.
Chemical Abstract 132:102809g. NAC inhibition of encephalomyelitis Theiler's virus-induced NO and TNF-a production by murine astrocyte cultures.
Chemical Abstract 132:136226e. Thiol regulation of the production of TNF-a, IL-6 and IL-8 by human alveolar macrophages.
Chemical Abstract 132:146456u. Antagonistic effects of pyrrolidine dithiocarbamate and NAC on surfactant protein A and B mRNA's.
Chemical Abstract 132:175757y. Pro-oxidant activity of flavonoids: copper-dependent strand breaks and the formation of 8-hydroxy-2'-deoxyguanosine in DNA.
Chemical Abstract 132:203095b. Inhibition of NO synthesis in primary cultured mouse hepatocytes by a-lipoic acid.
Chemical Abstract 132:246319v. Antioxidants protect against dopamine-induced metallothionein-III (GIF) mRNA expression in mouse glial cell line VR-2g.
Chemical Abstract 132:263131x. GSH redox system in oxidative lung injury.
Chemical Abstract 132:291636g. Adaptive response to swimming exercise: antioxidant systems and lipid peroxidation.
Chemical Abstract 132:318860q. Tobacco smoke induces mitochondrial depolarization along with cell death: effects of antioxidants.
Chemical Abstract 132:343761r. Epidermal growth factor and receptor is modulated by redox through multiple mechanisms. Effect of reductants and hydrogen peroxide.
Chemical Abstract 132:346458h. Redox regulation of chemokine receptor expression.
Gojon, Gabriel, Rrelative rate constants for hydrogen atom abstraction by the cyclohexanenthiyl and benzenethiyl radicals (Author's Disseration), Dec. 1974.
Sies, Helmut, Antioxidants in disease and therapy, Advances in Pharmacology vol. 38, Academic Press, San Diego, CA 1997.

* cited by examiner

SYSTEMIC TREATMENT OF PATHOLOGICAL CONDITIONS RESULTING FROM OXIDATIVE STRESS AND/OR REDOX IMBALANCE

CROSS-REFERENCE TO RELATED APPLICATIONS

This application is a divisional application of U.S. application Ser. No. 10/463,765 filed Jun. 18, 2003, which claims priority to U.S. Non-provisional Application No. 60/389,491 filed Jun. 19, 2002.

FIELD OF THE INVENTION

The present invention relates to novel compositions for and methods of treating symptoms, syndromes, pathological conditions and disease-associated problems mediated by oxidative stress. These conditions include cancer, AIDS, diabetes, cardiovascular diseases, Down syndrome, chronic inflammatory diseases, neurodegenerative diseases, cachexia secondary to HIV-1 infection, cachexia secondary to cancer and AIDS related complex (ARC), and hypercholesterolemia

BACKGROUND OF THE INVENTION

This application claims benefit of U.S. Provisional application Ser. No. 60/389,491, filed Jun. 19, 2002.

The present applicant serendipitously and unexpectedly discovered a therapy system useful for treating cancer, AIDS, cardiovascular diseases, Down syndrome, chronic inflammatory diseases, diabetes, neurodegenerative diseases and other disease states mediated by oxidative stress. This system comprises the delivery to the gut of a mammal of therapeutically effective amounts of one or more of the following active agents: sulfide compounds, thiosulfate compounds, thionite compounds, thionate compounds, and any organic, inorganic or organometallic precursors thereof.

The present applicant found in a preliminary evaluative clinical trial with far-advanced human cancer patients having histologically verified malignancies representing a wide range of cancer types (breast, colon, lung, prostate, larynx, testis, uterus, pancreas, muscle lymphoma, including lymphoma in the leg or gluteal muscles, carcinoma, sarcoma.) that a significant rate and extent of reduction in tumor size occurred, often followed by complete remission. The therapy system of the present invention substantially avoids several of the well-known problems and limitations of conventional cancer chemotherapy such as development of resistant malignant-cell variations, excessive concomitant toxicity, dependence on phase of cell cycle and mutagenic side effects.

In other preliminary clinical trials, the present applicant surprisingly found clear evidence of the effectiveness of essentially the same therapy system when applied to patients afflicted with Down syndrome, hypercholesterolemia and cardiovascular disease.

Although sulfur compounds have a long history of pharmaceutical usefulness, only two of the sets of compounds claimed in this application (thiosulfates and sulfites) have found wide use in pharmacology and/or in the formulation of final dosage forms as preservatives, antioxidants, or biocides. Thus, thiosulfates find application in the treatment of cyanide poisoning, allergic conditions and drug sensitization caused by gold, arsenic, mercury or bismuth preparations in humans, and in veterinary medicine as cyanide antidotes, as "general detoxifiers" and also in bloat and, externally, in treatment of ringworm or mange. Injection of aqueous solutions of sodium thiosulfate and L-cysteine or its sodium salt are claimed to be effective against "bacteria and viruses" in general. U.S. Pat. No. 4,148,885, issued to Renoux et al., discloses use of sodium thiosulfate and sodium metabisulfite as immuno-stimulants, but strictly within the context of "a process for stimulating the immunity of a living organism", although only mice are mentioned and only subcutaneous administration was employed.

Sulfites also display some pharmacological activity against the agents responsible for certain parasitic and infectious conditions. In addition German patent DE 3,419,686 discloses sulfite or bisulfite solutions for treating arthritis or epilepsy. PCT International Application WO 84/02527 claims increased anti-tumor activity for adriamycin and daunomycin with the addition of sulfites, acid sulfites, pyrosulfites and/or dithionites. U.S. Pat. No. 5,045,316, issued to Kaplan, claims that a combination of an ionic vanadium compound, a thiosulfate or sulfite, and optionally selenium is useful for treating malignant tumors, atherosclerosis and mental syndromes in the elderly. However, it should be clear that in the prior art neither thiosulfates nor sulfites have been claimed to act as herein disclosed by themselves or in admixture with each other and/or with sulfide compounds, thionite compounds, or thionate compounds, when delivered to a mammal in need thereof.

It should also be appreciated that both thiosulfates and sulfites are rapidly decomposed when released in the stomach, so that oral administration of aqueous solutions, tablets, or capsules containing sulfites or thiosulfates cannot be used for their delivery to the gut of a mammal, unless an enteric coating or an ad-hoc delivery system is employed. Exactly the same considerations apply to dithionites, which have been used (see above) in combination with adriamycin and daunomycin. On the other hand, sulfide compounds and thionate compounds have been, to the best of the present applicant's knowledge, neither claimed to act as herein disclosed nor hypothesized to be capable of such action when delivered to a mammal.

Without intending to be bound by any particular hypothesis or theory, current thinking on the etiology of cancer, AIDS, cardiovascular diseases, diabetes, Down syndrome, chronic inflammatory diseases and neurodegenerative disorders will be reviewed, in an attempt to understand the basis for the surprising success of the treatment method disclosed herein. Since the diverse sulfur compounds found by the present applicant to be pharmacologically active all possess reducing properties, special attention will be given to the possibility that a link exists between the two sets of properties and to research that bears on oxidation-reduction processes in cells, especially if it focuses on oxidative stress or its pathological manifestations.

In healthy human tissue a delicate balance between cell proliferation and cell death exists, which when disrupted can lead to a degenerative disease (diabetes and its vascular complications, anemia, arthritis, Parkinson's disease, Alzheimer's disease, Amyotrophic Lateral Sclerosis [A.L.S.], Huntington's disease, muscular dystrophy, myotonic dystrophy, chronic fatigue syndrome, Friedreich's ataxia, ocular lens opacification, nephrosis, liver necrosis, dermatitis, pulmonary immune deficits, hepatic encephalopathy, macular degeneration, age-associated memory impairment, Creutzfeldt-Jacob's disease, stroke, epilepsy, peripheral neuropathy, optic neuropathy, anatomic neuropathy, Neutrogena bowel disease, sensorineural deafness, neurogenic bladder dysfunction, migraine, renal tubular acidosis, dilating cardiomyopathy, hepatic failure, lactic acidemia, arsenic poisoning, silicosis, acetaminophen poisoning, asbestosis, asthma, rheumatic polyarthritis, ARDS adult respiratory distress syndrome) in case of premature cell loss. Similarly, disruption of this balance can lead to a hyperproliferative disease (cancer, AIDS, herpes simplex virus-1 infection, cytomegalovirus-induced vascular pathology, arteriosclerosis, ARC, hepatitis, trypanosomiasis, vascular restenosis, psoriasis, glomerular nephritis, transplant rejection, etc.) in case of cell over-accumulation. It must be pointed out that mitochondrial function is the key to this balance, since mitochondria regulate apoptosis, the physiological mechanism for the elimination of cells in a controlled and timely manner.

The defense mechanism of a mammal (humoral/cellular immunity mediated by non-phagocytic lymphocytes, phagocytic polymorphonuclear leucocytes, and voraciously phagocytic monocytes/macrophages) eliminates foreign bodies such as microorganisms (bacteria, rickettsias, viruses, fungi, protozoa or metazoa) and abnormal cells, including neo-formed cells capable of becoming a cancerous tumor such as a carcinoma, sarcoma, myoma or lymphoid tumor through hyperproliferation.

Cancerous tumors are usually life-threatening; in humans they include, among others, prostate, colon, breast, lung, kidney, liver, lymphoma of the central nervous system (CNS), leukemia, pancreatic, gastric, esophageal, ovarian, uterine, testicular and skin tumors. Most human and animal cancer involves cells of epithelial origin, whose malignant transformation results in carcinomas, i.e., tumors of epithelial cell origin.

The balance between cell proliferation and cell death in a healthy mammal depends critically on both an intact immune system, and a finely tuned systemic balance between antioxidants and oxidants, which will be referred to hereinafter as "redox homeostasis". Moreover, redox homeostasis is also essential for the components of the immune system to function adequately.

Stepwise reduction of molecular oxygen (dioxygen) to water inside mammalian cells is the source of the ATP needed by the cell to power its multiple activities. However, the partially reduced intermediates formed during this process (superoxide radical anion, hydrogen peroxide, hydroperoxy radical and hydroxy radical) are highly reactive and their leakage can be the cause of oxygen toxicity, oxidative stress, and/or oxidative damage to biomolecules and complex cell structures such as membranes and mitochondria; these partially reduced species are known collectively as "reactive oxygen intermediates" (R.O.I.).

Furthermore, some cells belonging to the immune system generate hypochlorous acid or R.O.I.'s ("respiratory burst") in order to use them as weapons against foreign bodies. Detoxication of xenobiotics (including drugs) is another common source of R.O.I.'s, as well as the enzymatic synthesis of prostaglandins, thromboxanes, and leukotrienes from polyunsaturated fatty acids in epithelial cells.

During the last decade, it has become evident that R.O.I.'s perform an extremely important direct role in signal transduction; most sources of the R.O.I.'s involved in signal transduction seem to initially generate superoxide, whose disproportionation then yields hydrogen peroxide. As noted by Powis et al. ("Redox signaling and the control of cell growth and death", in Helmut Sies (ed.) "Antioxidants in disease mechanisms and therapy", Academic Press, 1997), intracellular redox signaling is the result of controlled changes in the intracellular redox state. This signaling can regulate the cell cycle, including the control of DNA synthesis, enzyme activation, and gene expression. The redox signaling operates by changing the conformation of key proteins by changing the oxidation state of cysteine residues in these proteins. These conformational changes affect the biological function of the protein. These conformationally sensitive proteins directly affect cell growth and differentiation, as well as cellular apoptosis.

A variety of experimental results, reported between 1994 and 2000, illustrate the importance of redox status/R.O.I.'s in cellular signaling systems and mammalian health. Metallothionein-III (MT-III) is a brain-specific metallothionein, which is markedly reduced in the brain of patients with Alzheimer's disease (AD) and other degenerative diseases. Oxidative stress seems to be one of the principal factors that modulate MT-III mRNA (Messenger Ribonucleic Acid) expression. Pulmonary surfactant, a mixture of phospholipids and surfactant proteins (SP-A and SP-B) reduces surface tension at the air-liquid interface and protects the large epithelial surface of the lung from infectious organisms. Cellular oxidants reduce surfactant protein expression. Also, antioxidants reduce cyclooxygenase-2 expression, prostaglandin production and proliferation in colorectal cancer.

Overexpression of mdr-1 type transporters in tumor cells contributes to multidrug-resistance. The induction of mdr-1bmRNA and of functionally active mdr1-type P-glycoprotein by elevation in intracellular levels of reactive oxygen species and the repression of intrinsic mdr-1bmRNA and P-glycoprotein overexpression by antioxidants support the conclusion that the expression of the mdr-1b P-glycoprotein is regulated in a redox-sensitive manner.

Oxidative stress regulates the expression of various regulatory genes in rabbit lens epithelial cells, which likely affects cell proliferation, differentiation, and viability and thus affects normal cell function [CA 127:230414h].

In cultured keratinocytes, Butylated Hydroxytoluene Hydroperoxide (BHTOOH) stimulates a time-dependent increase in ornithine decarboxylase (ODC) enzyme activity paralleled by induction of ODCmRNA (mRNA that directs ODC synthesis), suggesting transcription regulation of ODC by BHTOOH. Depletion of intracellular glutathione caused a 5-fold potentiation of keratinocyte sensitivity to BHTOOH and consequently, of tumor promotion.

R.O.I.'s can also act indirectly as signal transducers by modifying the bioavailability of nitric oxide (NO); thus, inflammatory cytokines such as Tumor Necrosis Factor-α (TNF-α) and interleukins (IL's) induce NO (nitric oxide) overproduction. NO is a messenger endogenously synthesized by a variety of mammalian cells including neurons, smooth muscle cells, macrophages, neutrophils, and platelets. In fact there is cross-talk between R.O.I.'s and NO, since the effects of the latter are influential on signaling pathways regulated by thiolic redox status.

However, if superoxide and NO interact a powerful non-radical oxidant, peroxynitrite (PN), is readily formed. PN is capable of oxidizing a number of biomolecules and complex cell structures including enzymes such as catalase and glutamine synthetase, proteins containing tyrosine residues, DNA, brain mitochondria and membrane lipids such as synaptosomal membranes.

NO itself has been implicated in a variety of neurodegenerative disorders and is a mediator in excitotoxic and post-hypoxic damage to neurons. DNA strand breakage is induced synergistically by NO and a catecholamine.

Most living organisms have evolved well-integrated antioxidant defense mechanisms, which include both antioxidant enzymes such as catalase, superoxide dismutases, glutathione peroxidases, quinone reductase, diaphorase and ceruloplasmin and low molecular weight antioxidants (LMWAO's) such as pyruvic acid, glutathione (GSH), dihydrolipoic acid (DHLA), beta-carotene, vitamin C, vitamin E and thioredoxin (TRX, a ubiquitous, relatively small, dithiolic, hydrogen-carrier protein).

Whereas antioxidant vitamins and beta-carotene must be supplied through food intake (e.g. in fruits and vegetables), both the thiolic tripeptide glutathione and DHLA are endogenous antioxidants, as well as pyruvic acid.

Pyruvic acid, being a normal tissue metabolite, is likely to be non-toxic and its high effectiveness as a "peroxide scavenger" is well documented; furthermore, after scavenging hydrogen peroxide or organic hydroperoxides it is converted into acetic acid, which means that it is intrinsically incapable of acting as a prooxidant. In spite of these attributes, pyruvic acid's role as an endogenous antioxidant has been widely underestimated: it is probably an important but underrated contributor to the "redox buffering" capacity of blood serum.

Glutathione (L-gamma-glutamyl-L-cysteinylglycine) is a ubiquitous intracellular thiol present in almost all mammalian tissues; the liver has very high intracellular levels of GSH.

Besides maintaining cellular integrity by enforcing a reducing environment, GSH has multiple functions including detoxication of xenobiotics; synthesis of proteins, nucleic acids, leukotrienes, prostaglandins and thromboxanes through its action as a coenzyme; and preventing other antioxidants from becoming pro-oxidants.

GSH enforces a reducing intracellular environment by acting as an excellent scavenger of both oxygen-centered and nitrogen-centered free radicals (reactive nitrogen intermediates, RNIs) and by readily converting non-radical oxidants (PN, peroxides, hydroperoxides) into harmless compounds. After acting as a coenzyme or scavenging R.O.I.'s or PN, GSH is oxidized to GSSG (glutathione disulfide), from which GSH is regenerated enzymatically. The redox system of GSH consists of primary and secondary antioxidants, including glutathione peroxidases, glutathione reductase, glutathione-S-transferase, and glucose-6-phosphate dehydrogenase.

Redox reactions in which GSH plays a role include protein folding, conversion of ribonucleotides to desoxyribonucleotides, and maintenance of reduced pools of vitamins C and E; GSH can also undergo reversible thiol-disulfide exchange with proteins containing oxidized cysteine (i.e., cystine) residues.

Whereas in tissues and red blood cells (CA 131:156247v) GSH is the foremost "redox buffer", in blood plasma this function has been assigned to albumin, although this applicant believes that pyruvic acid is also a key antioxidant in both environments.

As stated above, DHLA and thioredoxin perform roles that complement those of GSH; their oxidized forms can also be reduced easily by enzyme action. Vitamins C and E, which can readily and reversibly act as hydrogen donors as well, also contribute to maintain the intracellular oxidant-reductant balance (redox homeostasis).

By operating in a concerted and often synergistic manner, the redox mediators GSH, DHLA, TRX, Vitamin C, Vitamin E, and the antioxidant enzymes help maintain a reducing intracellular environment. This reducing environment performs a variety of important cellular functions. First, it helps keep bioactive quinones in the reduced state. For example, cardiotonic ubiquinones and vitamin K are maintained in their reduced state (ubiquinol/hydroquinone), so as to minimize the probability of arylating DNA and of generating R.O.I.'s in anaerobic or aerobic conditions. Also, it keeps catecholamines (adrenaline, dopamine, etc.) in the reduced (hydroquinone) condition, preventing their irreversible oxidation to quinoneimines of the adrenochrome type. The reducing intracellular environment also prevents vasoactive serotonin from being oxidized to a reactive quinoneimine.

The reducing intracellular environment prevents inactivation of heart dihydrolipoamide dehydrogenase and of other oxidant-sensitive enzymes such as glutamine synthetase. The reducing environment attenuates hypersensitivity responses induced by oxidative activation of phenolic haptens, and preserves the functional integrity of the blood-brain barrier, of the intestinal epithelium, and of the heart endothelium. It also helps preserve cytoskeletal integrity. The reducing environment protects synaptosomal membranes from oxidation, and prevents the death of hippocampal neurons. It is also important to phagocytes, as it supports their random migration, chemotaxis, ingestion and superoxide production.

Of particular significance is the role of a reducing environment in preserving the functional integrity of mitochondria. GSH and Glutathione peroxidase (GPx) play a critical role here, since mitochondria lack catalase, an enzyme which degrades hydrogen peroxide. "Mitochondrial diseases" are disorders to which deficits in mitochondrial respiratory chain activity contribute. This category includes deficiencies in the activity of components of the mitochondrial respiratory chain. Typically, these deficiencies are caused by exposure of the cells to nitric oxide and hypoxia or ischemia or oxidative stress on the tissue. These deficiencies in antioxidants or antioxidant enzymes can result in or exacerbate mitochondrial degeneration. It must be pointed out that redox homeostasis also requires a delicate antioxidant enzyme balance in cells: too much Superoxide Dismutase (SOD) relative to GPx or catalase results in the accumulation of hydrogen peroxide, which in turn, through the Fenton reaction, leads to the production of hydroxyl radical and concomitant cell damage; however, too little SOD enzyme is also not favorable because superoxide radicals in themselves are toxic to cells. Therefore, fine-tuning of the antioxidant enzymes. (together with the nonenzymatic antioxidants) becomes imperative if the cell is to function successfully in an oxygen-rich environment.

Down syndrome is believed to be the consequence of a congenital perturbation in the balance of antioxidant enzymes, with damage to important biomolecules brought about by a highly pro-oxidant intracellular environment.

In the face of stresses such as injury or infection, organisms rapidly marshal a host of responses: immune cells are recruited and various genes are rapidly activated. The key coordinating factor in this activation is the nuclear transcription factor NF-κB, which also plays a crucial role in modulating gene expression during growth and development.

Among the genes modulated by NF-κB are those encoding cytokines (TNF-α, IL's, etc.) and growth factors, immunoreceptors, adhesion molecules, acute-phase proteins, other transcription factors and regulators, NO-synthase, and viral genes. Most target genes for NF-κB are intrinsically linked to a coordinated inflammatory response.

NF-κB has far-reaching significance for a variety of pathological conditions in which inflammation, growth, or viral activation occur, such as tumor genesis, HIV infection (AIDS), atherosclerosis, diabetes, rheumatoid arthritis, chronic bronchitis, cystic fibrosis, idiopathic pulmonary fibrosis, ARDS, septic shock, cirrhosis, ulcerative colitis, reperfusion injury, inflammatory bowel disease, pulmonary emphysema, neurodegenerative disorders, (Alzheimer's Disease, Parkinson's Disease, etc.), osteoporosis, asthma, renal disease, rheumatoid synovitis, and the animal model of multiple sclerosis, experimental allergic encephalomyelitis.

An important NF-κB regulated gene is that encoding the cytokine TNF-α which plays a central role in several inflammatory conditions. Since TNF-α is itself an activator of NF-κB, the potential for a positive inflammatory feedback cycle with disastrous consequences can be envisioned.

As stated above, the activation of NF-κB has been implicated in a wide range of diseases in which there is an inflammatory and/or hyperproliferative component including AIDS, where the expression of HIV is NF-κB dependent. It is now clear that ROI/RNI are mediators of NF-κB activation, and also that this process can be blocked by antioxidant agents.

Antioxidant agents can also inhibit the production of TNF-α. Excessive or unregulated TNF-α production mediates or exacerbates a number of diseases including rheumatoid arthritis, rheumatoid spondylitis, osteoarthritis, gouty arthritis, sepsis, septic shock, endotoxic shock, gram-negative sepsis, toxic shock syndrome, Adult Respiratory Distress Syndrome (A.R.D.S.), cerebral malaria, chronic pulmonary inflammatory disease, silicosis, asbestosis, pulmonary sarcoidosis, bone resorption diseases, reperfusion injury, graft vs. host reaction, allograft rejections, cachexia secondary to infection or malignancy, cachexia secondary to acquired immune deficiency syndrome (AIDS), AIDS, AIDS related complex, keloid formation, scar tissue formation, Cohn's disease, ulcerative colitis, pyrosis and fever and myalgias due to infection.

Although most experts would admit the possibility that "the time course and even the final outcome, of a disease can be critically modulated by strengthening the antioxidant side of the balance between prooxidants and antioxidants, it is unfortunately true that single antioxidants as pharmacologically active agents have not been found to exhibit extremely powerful therapeutic effects. For example, the jury is still out regarding the effectiveness of vitamin C as a therapeutic agent. Nevertheless, vitamin C may have a role in impeding the progress of diabetes, cataract, heart disease, cancer, aging, and a variety of other disease states. Several methods for modulating cellular GSH levels in human diseases associated with GSH deficiency and oxidative stress are still being evaluated. DHLA, regarded in some quarters as a unique "ideal" antioxidant remains an intriguing possibility for the treatment of conditions (notably AIDS, atherosclerosis and diabetes) related to oxidative stress.

Treatment of severe vitamin E deficiency with appropriate supplements of the vitamin can at least halt the progression of the characteristic neurological features, but in the majority of clinical neurological conditions the therapeutic benefits of antioxidant supplementation still requires to be proved. On the other hand, vitamin E has been reported to regress oral leukoplakia (a precancerous lesion). Supplemental beta-carotene reduces the frequency of "oral micronuclei" (an indicator of genotoxic damage to the oral epithelium) significantly; it is also effective against oral leukoplakia. Preliminary results of studies on pre-cachectic and cachectic HIV-infected patients indicate that the decrease of plasma cystine, glutamine, and arginine levels can be corrected by N-Acetyl-L-Cysteine (NAC). Anecdotal data also suggest that this strategy may slow or even prevent the progression of the disease.

A preliminary report indicates that ARDS patients receiving NAC (po [by mouth]), □-tocopherol (po), selenium (iv. [intravenous]), and ascorbic acid (iv.) within 24 hrs. of diagnosis for 3 days experienced a significant reduction in mortality (n=25; 20% mortality) compared to a control group (n=20; 65% mortality); however, these results are in need of validation.

Finally, a randomized trial (n=65) with biopsy-confirmed transitional cell bladder carcinoma patients yielded promising results: the 5-year estimate of tumor recurrence was 91% in the "RDA arm" (patients receiving multivitamins at RDA (Recommended Daily Allowance) levels) vs. 41% in the "megadose arm" (patients receiving multivitamins at RDA levels plus 40,000 IU retinol plus 100 mg pyridoxine plus 2000 mg ascorbic acid plus 4000 IU alpha tocopherol plus 90 mg zinc).

This rather limited success might seem at first surprising in view of the decreased levels of selected major antioxidants consistently found in a number of disease states (GSH in AIDS, hepatitis C, type II diabetes, ulcerative colitis, A.R.D.S., idiopathic pulmonary fibrosis and neurodegenerative syndromes; vitamin E in atherosclerosis, ARDS, Down syndrome and Alzheimer's disease; ascorbic acid in ARDS; beta-carotene in cystic fibrosis; vitamin A in Down syndrome and Alzheimer's disease, etc.). On second thought, however, the limited success of this "magic single antioxidant approach" can be rationalized by recalling that mammals possess highly evolved and well-integrated antioxidant mechanisms which require the concerted and synergistic action of both antioxidant enzymes and low molecular weight antioxidants, with different antioxidants operating extracellularly and/or in specific cell compartments (aqueous vs. lipidic microenvironments) and having limited functional overlap. Some antioxidants destroy peroxidic species and/or PN, others break free radical chains; still others quench singlet oxygen.

There are other foreseeable obstacles in the way of the "single antioxidant" approach to therapy. Several antioxidants have been shown to be capable of acting as pro-oxidants or as NF-κB activators "in vitro" and/or "in vivo" under rather specific conditions, including ascorbic acid, beta carotene, glutathione, flavonoids, NAC, and L-cysteine. Limited evidence suggests that administration of a single antioxidant might have adverse effect(s) on plasma levels of other antioxidants.

After this appraisal of the current biochemical research on the etiology of cancer, AIDS, cardiovascular diseases, diabetes, Down syndrome, neurodegenerative disorders and chronic inflammatory diseases, the following hypotheses might help explain the remarkable success of the therapy system herein described:

The sulfur compounds comprised by the therapy system herein disclosed act as inducers of antioxidant enzymes, thereby enhancing the immune system and/or reactivating mitochondria and/or increasing GSH levels, i.e. their effects are similar to those of 1,2-dithiole-3-thiones. The sulfur compounds herein disclosed act as powerful antioxidant enzyme activators. Specifically, they interact chemically, as reductants, with inactivated enzymes containing disulfide bonds which are thereby cleaved and converted into thiol groups with concomitant restoration of enzyme function. In this case their effect would be akin to that of hydrogen sulfide on inactivated (oxidized) papain. The sulfur compounds on which the present invention is based (excepting sulfides and hydrosulfides) act indirectly through the delivery of "reducing equivalents" to cells subject to oxidative stress, their effect being restoration of redox homeostasis and immune function. The mediator might well be pyruvic acid (see above) since it is known that pyruvic acid can act systemically when delivered to the gut; i.e. it can be readily transported from the gut to other tissues. Further, pyruvate has been shown to enhance the endogenous GSH system Also, there is a linear relationship between GSSG-to-GSH and lactate-to-pyruvate ratios in human blood before, during and after exercise.

In a study on the nutritional requirements of human gut sulfate-reducing bacteria, it was found that short-chain fatty acids such as butyric acid, lactic acid, and other organic acids; alcohols; and amino acids (but not sugars or aromatic compounds) stimulated sulfate reduction. Experiments with two strains of desulfovibrio desulfuricans isolated from human feces demonstrated that both were able to reduce sulfite, thiosulfate or nitrate in the absence of sulfate.

Therefore, while the present invention is not to be restricted by any hypothesis, it is possible that pyruvate, synthesized in the gut by bacterial microflora from lactate and sulfite or thiosulfate (or some other sulfur species capable of undergoing reduction), is then transported to the mammal's tissues, wherein it acts, mainly at the mitochondrial level, as a peroxide scavenger and a source of both NADH and energy (via acetyl coenzyme A); NADH (reduced nicotinamide adenine dinucleotide) can enzymatically reduce lipoic acid (LA) to DHLA, which can in turn reduce GSSG to GSH.

Considering the seriousness of the AIDS pandemic, the global burden of cancer (with close to 10 million newly diagnosed cases each year), and the devastating effects of such diseases as diabetes, chronic inflammatory diseases, neurodegenerative pathologies, and Down syndrome it is clear that a pressing need exists for effective treatments of pathological states related to oxidative stress and/or exacerbated or mediated by NF-κB/TNF-α, such as the ones referred to above. This becomes even more clear when we consider the fact that cardiovascular diseases (and atherosclerosis, which is believed to be their underlying primary cause) are the main cause of death in most developed countries.

SUMMARY OF THE INVENTION

This invention relates to a novel method useful for treating cancer, AIDS, ARC, cachexia secondary to AIDS, cachexia secondary to cancer, diabetes, Down syndrome, cardiovascular diseases, Hypercholesterolemia and neurodegenerative diseases. This novel method, useful for treating said disease conditions, comprises the delivery of therapeutically-effective amounts of the following compounds, either individually or intermixed: sulfide compounds, thiosulfate compounds, thionite compounds, sulfite compounds, and thionate compounds to the gut of a mammal in need thereof.

This invention further comprises treatment by parenteral administration of thiosulfate compounds and/or thionate compounds and, optionally, other active agents to a patient (or non-human mammal) afflicted with cancer, AIDS, ARC, cachexia secondary to cancer, cachexia secondary to AIDS, diabetes, Down syndrome, cardiovascular disease or a neurodegenerative disease.

This invention further comprises treatment of a patient (or non-human mammal) afflicted with cancer, AIDS, ARC, cachexia secondary to cancer, cachexia secondary to AIDS, diabetes, Down syndrome, cardiovascular disease or a neurodegenerative disease by administration of therapeutically-effective amounts of a least one of the compounds herein disclosed by any means that produces contact of the active agent or agents with their site of action in the mammal's body.

This invention also relates to pharmaceutical compositions comprising one or more of the above-mentioned compounds, or pharmaceutically acceptable organic, inorganic or organometallic precursors thereof, and one or more pharmaceutically acceptable excipients, carriers, diluents or adjuvants.

This invention further relates to a method for preparing pharmaceutically acceptable dosage forms containing the aforementioned ingredients and capable of releasing the pharmacologically active ingredient or ingredients in the gut of a mammal in need thereof.

The present invention also comprises the use of combination therapies involving administration of the aforementioned active ingredients.

The present invention further comprises administering one of the formulations herein described to non-human mammals, i.e. as veterinary medication for treatment of said non-human mammals in need thereof.

DETAILED DESCRIPTION

Definitions

Sulfide compounds are compounds formally containing the divalent $S_n$ moiety (S=sulfur; n=1, 2, 3 . . . ) chemically bonded to hydrogen and/or a metal (or metals) and/or a polyatomic cation (or cations) such as hydrogen sulfide, hydrogen disulfide, hydrogen tetrasulfide, sodium hydrosulfide, sodium hydrosulfide dihydrate, sodium sulfide, sodium sulfide nonahydrate, potassium sulfide, calcium sulfide, iron(II) sulfide, silicon (IV) sulfide, zinc sulfide, bismuth (III) sulfide, sodium disulfide, magnesium disulfide, iron (II) disulfide, sodium tetrasulfide, barium tetrasulfide, potassium pentasulfide, cesium hexasulfide, potassium iron (III) sulfide, ammonium sulfide, ammonium disulfide and ammonium tetrasulfide.

Sulfite compounds are compounds formally containing the divalent sulfite moiety (SO3) chemically bonded to hydrogen, and/or a metal (or metals) and/or a polyatomic cation (or cations), such as sodium sulfite, potassium sulfite, ammonium sulfite, calcium sulfite, and cesium hydrogensulfite.

Thiosulfate compounds are compounds formally containing the divalent thiosulfate moiety (S2O3) chemically bonded to hydrogen and/or a metal (or metals) and/or a polyatomic cation (or cations), such as sodium thiosulfate (Na2S2O3), sodium thiosulfate pentahydrate (Na2S2O3.5H2O), magnesium thiosulfate (MgS2O3), silver thiosulfate (Ag2S2O3), ammonium thiosulfate [(NH4)2S2O3].

Thionate compounds are compounds formally containing the divalent SnO6 (n>1) moiety chemically bonded to hydrogen and/or a metal (or metals) and/or a polyatomic cation (or cations), such as calcium dithionate (CaS2O6), barium dithionate dihydrate (BaS2O6.2H2O), sodium trithionate and sodium tetrathionate.

Thionite compounds are compounds formally containing the divalent SnO2n (n=1 or 2) moiety chemically bonded to a hydrogen and/or a metal (or metals) and/or a polyatomic cation (or cations) such as zinc sulfoxylate, zinc dithionite, sodium dithionite and sodium dithionite dihydrate.

Organic, inorganic or organometallic precursors of the previously defined compounds are any and all chemical species from which sulfide compounds and/or thiosulfate compounds and/or thionite compounds and/or thionate compounds, can arise through chemical change and/or enzyme action and/or biotransformation in a mammal's body. Therefore, tetraphosphorus decasulfide (P4S10) and sodium thiosilicate (Na2SiS3) are precursors of sulfide compounds.

Active sulfur compounds, as defined in the current invention, encompass:

1) sulfide compounds, 2) thiosulfate compounds, 3) thionate compounds, 4) thionite compounds, and 5) organic, inorganic or organometallic precursors of sulfide compounds, thiosulfate compounds, thionate compounds, and thionite compounds.

Treatment by delivery to the gut of a mammal of therapeutically effective amounts of the active ingredient(s) includes:

a) Administration of a solution or dispersion of the active ingredient(s) by enteroclysis.

b) Oral administration of enterically coated tablets, granules, capsules, etc. which contain the active ingredient(s) and (optionally) one or more carriers and/or diluents and/or adjuvants. The composition may be administered in the form of tablets coated with an enteric coating; capsules having a shell, a filling comprising the active ingredient, and an enteric coating on the shell; or enterically coated granules comprising the active sulfur compound. The enterically coated granules may be included within a tablet, or as a filling within a capsule.

c) Oral administration of non enterically-coated capsules containing the active ingredient(s) and (optionally) one or more carriers and/or diluents and/or adjuvants absorbed and/or adsorbed on an inert substrate such as microcrystalline cellulose.

d) Oral administration of delayed-release formulations containing the active ingredient(s) and (optionally) one or more carriers, diluents and adjuvants.

e) Rectal administration, as by using suppositories containing the active ingredient(s) and (optionally) one or more carriers, diluents and adjuvants.

f) Coadministration of the active ingredient (s) with any other pharmacologically active agents such as vitamins, micronutrients, coenzyme Q10, glucosamine, chondroitin sulfate, triiodothyronine, vinpocetine, pramiracetam, piracetam, hydergine, choline, niar, gallic acid, diallyl sulfide, anti-cancer agent (s), immunostimulant (s), antibiotic(s), hormone antagonist (s), antiviral agent(s), antihypertension agent(s), insulin and anti-inflammatory agent (s), optionally including one or more vehicles, carriers, diluents and adjuvants either orally [as in b), c), or d) above] or by enteroclysis [as in a) above] or rectally [as in e) above].

Parenteral administration to a patient (or non-human mammal) includes:

a) Intravascular administration of solutions/dispersions containing at least one of the compounds herein disclosed and, optionally, other active agents and/or one or more adjuvants.

b) Intramuscular administration of solutions/dispersions containing at least one of the compounds herein disclosed and, optionally, other active agents and/or one or more adjuvants.

c) Subcutaneous administration of solutions/dispersions containing at least one of the compounds herein disclosed and, optionally, other active agents and/or one or more adjuvants.

d) Intrathecal administration of solutions/dispersions containing at least one of the compounds herein disclosed and, optionally, other active agents and/or one or more adjuvants.

e) Transdermal administration of appropriate formulations containing at least one of the compounds herein disclosed and, optionally, other active agents and/or one or more adjuvants.

f) Transmucosal administration of appropriate formulations containing at least one of the compounds herein disclosed and, optionally, other active agents and/or one or more adjuvants.

g) Sublingual administration of appropriate formulations containing at least one of the compounds herein disclosed and, optionally, other active agents and/or one or more adjuvants.

The term mammals is intended to mean both human and non-human mammals.

As used herein, therapeutically-effective amount refers to that amount that must be administered per day to a patient (on non-human mammal) in order to achieve an anti-tumor effect; to modulate an immune response; to modulate gene expression; to ameliorate Down syndrome; to treat hypercholesterolemia; to treat leukemia; or to treat cardiovascular disease. Methods of determining therapeutically effective amounts are well known.

By disease-associated problem is meant a health problem derived from a specific disease, such as "cachexia secondary to cancer" or "muscle degeneration secondary to AIDS".

As used herein, gut means intestine.

As used herein, a pharmaceutically acceptable component is one that is suitable for use with humans and/or non-human mammals without undue adverse side effects (such as toxicity, irritation and allergic response) commensurate with a reasonable benefit/risk ratio.

By safe and effective amount is meant the quantity of a composition which is sufficient to elicit a desired therapeutic response without undue adverse side effects (such as toxicity, irritation or allergic response) commensurate with a reasonable benefit/risk ratio when used in the manner of this invention.

As used herein, combination therapy means that the patient (or non-human mammal) in need of treatment according to the present invention, is given medication not herein contemplated in addition to that herein disclosed. Combination therapy can be sequential therapy" where the patient or non-human mammal is treated first with one or more drugs and then the other(s), or simultaneous therapy, when all drugs are co-administered.

Mitochondrial diseases are disorders to which deficits in mitochondrial respiratory chain activity contribute. This category includes:

a) Congenital genetic deficiencies in activity of one or more components of the mitochondrial respiratory chain, and b) Acquired deficiencies in the activity of one or more components of the mitochondrial respiratory chain, wherein such deficiencies are caused by, inter alia, oxidative damage during aging, and/or exposure of affected cells to NO.

Finally, a number of abbreviations are used in this application. The abbreviation ASK, as used herein, relates to the protein apoptosis signal-regulating kinase. The abbreviation I.U. refers to International Unit. The abbreviation LTR relates to the phrase long terminal repeat, while mdr relates to multiple drug resistance.

Treatment Method

The applicant has demonstrated that delivery to a patient (or non-human mammal) afflicted with cancer, hypercholesterolemia/cardiovascular disease, or Down syndrome of safe and effective amounts of the compositions herein disclosed constitutes an effective treatment method.

In cancer patients, treatment in accordance with this invention will usually bring about a rapid and marked reduction of tumor size: such size reduction is characteristic clinical evidence for malignant cell death and degeneration (oncolysis); a similar reduction in malignant cell content of tissues containing disperse (nonaggregated) malignant cells will also usually result from treatment carried out as prescribed in this invention. In fact, dosage should be closely monitored to avoid any side effects due to either medication toxicity or massive release of toxins by malignant cell's lysis; it may be preferable to treat in short courses of several days, leaving a few days in between.

In acute situations the patient or non-human mammal can be given a high initial "loading dose", followed by a 50% lower "maintenance dose".

In every instance close monitoring of the patient or non-human mammal is necessary, especially upon initial administration of any of the formulations herein disclosed, since a mild or severe allergic reaction (including anaphylactic shock) might ensue in susceptible individuals. Although such allergic reaction was not observed in any of the numerous patients treated thus far, it is a well-known fact that oral administration of sulfites and metabisulfites has provoked this kind of reaction (asthmatic episodes, for instance) in susceptible individuals.

Fortunately, sulfite susceptibility among the general population is probably very low, since "sulfite compounds" are widely used as "pharmaceutical aids" (antioxidants) in many types of dosage forms for oral administration ("The Merck Index" 12$^{th}$ Edition, monograph #8784, Merck and Co., 1996). However, it is also known that the prevalence of sulfite susceptibility among asthmatic patients is higher than among the general population; therefore it is advisable to ensure that patients in this "high risk" group be screened and declared not susceptible to orally-administered sulfites before treatment is instituted.

It will be envisaged by those skilled in the art that the actual daily dosages of the foregoing compositions to be administered to a patient or to a non-human mammal will lie entirely within the discretion of the physician or veterinarian, as the case might be. Thus, the daily dosage for an adult human male of average weight (i.e. about 70 Kg) should be greater than that for a child (or for a non-human mammal of lesser weight than the average human male) if other factors are equal, but the converse would be expected when dealing with e.g. either humans or non-human mammals heavier than the average human male.

Additionally, of course, the appropriate dosage administered in any given case will vary with the age, general health condition, nature and extent of symptoms and nature of concurrent treatment (if any).

In all cases, treatment must be adjusted as required on the basis of frequent individual clinical evaluations, with due consideration of appropriate test results.

The preferred dosage levels are about 1 capsule per 2 Kg of patient (or non-human mammal) weight per day for all the compositions herein disclosed but—as discussed above— should be adjusted on an individual basis, and may be increased by a factor of up to about 5 or decreased by a factor of up to about 10 if deemed necessary.

EXAMPLES

The invention can be illustrated by the following non-limitative examples:

Formulation Example 1

Two hundred and fourteen (214) parts by weight sodium hydrogen sulfide (NaSH), six hundred and forty (640) parts by weight distilled water and two thousand (2000) parts by weight food grade microcrystalline cellulose were thoroughly blended at room temperature. The final powdery mixture was used for filling standard, two-piece hard gelatin capsules with 1,000 milligrams per capsule.

Formulation Example 2

Three hundred and seventy two (372) parts by weight sodium thiosulfate (Na2S2O3), six hundred and forty (640) parts by weight distilled water and two thousand (2000) parts by weight food grade microcrystalline cellulose were thoroughly blended at room temperature. The resulting powdery mixture was used for filling standard two-piece hard gelatin capsules with 1,000 mg per capsule.

Formulation Example 3

Four hundred and sixty four (464) parts by weight potassium metabisulfite (K2S2O5), six hundred and forty (640) parts by weight distilled water and 2,000 parts by weight food grade microcrystalline cellulose were thoroughly blended at room temperature. The resulting powdery mixture was used for filling standard, two-piece hard gelatin capsules with 1,000 mg per capsule.

Formulation Example 4

One-thousand five-hundred and thirty-two (1532) parts by weight sodium thiosulfate (Na2S2O3), two-hundred and thirty-two (232) parts by weight potassium metabisulfite, two-hundred and twelve (212) parts by weight sodium metabisulfite, four hundred and eighteen (418) parts by weight sodium sulfide nonahydrate 1090 parts by weight distilled water and 2000 parts by weight food-grade microcrystalline cellulose were thoroughly blended at room temperature. The resulting powdery mixture was used for filling standard, two-piece hard gelatin capsules with 1,000 milligrams per capsule.

Utility Example 1

Patient: Male, 74 year-old.
Baseline condition: Scarcely differentiated epidermoid larynx carcinoma associated with severe necrosis. The tumor is not operable on account of patient's marked cachexia and critical cardiovascular condition. Patient's status diagnosed as terminal.
Treatment regime: Administration of 24 capsules per day, each containing 1000 mg. of a formulation prepared as in "formulation example 1" (approximately 75 mg. of active ingredient and 925 mg of inert ingredients).
Treatment outcome: At the end of the first week, tumor size was halved; at the end of the third week, tumor size was one fourth of original size.

Utility Example 2

Patient: Male, 15 year-old.
Baseline condition: Acute lymphocytic leukemia refractory to conventional chemotherapy.
Patient's status diagnosed as terminal.
Treatment regime: Administration of 18 capsules per day, each containing 1000 mg of a mixture prepared as in "formulation example 2" (approximately 125 mg of active ingredient and 875 mg of inert ingredients).
Treatment outcome: At the end of the second week, patient's blood count (leucocytes, erythrocytes and platelets) presented an alarming reduction, associated with a critical condition that required several blood transfusions.
At the end of the third week patient's condition was stable, presenting a normal blood count and a reduction in blast count from 90% to 38%.
At the end of the fourth week, all blood parameters were normal (including a zero blast count). Patient's status diagnosed as normal with total remission.

Utility Example 3

Patient: Male, 38 year-old.
Baseline condition: Seminoma refractory to radiotherapy and to conventional chemotherapy.
Treatment regime: Administration of 30 capsules per day, each containing 1000 mg of the mixture prepared as in "formulation example 3" (approximately 150 mg of active ingredient and 850 mg of inert ingredients).

Treatment outcome: At the end of the first week, the persistent pain in the remaining testicle disappeared and the consistency of the testicle was almost normal.

At the end of the sixth month patient's status was diagnosed as normal with total remission.

Utility Example 4

Patient: Male, 63 year-old.

Baseline condition: Colon carcinoma. The tumor's size precludes surgery. Patient's status diagnosed as terminal.

Treatment regime: Administration of 24 capsules per day, each containing 1000 mg of a formulation prepared as in "formulation example 4" (approximately 280 mg of sodium thiosulfate, 42 mg of potassium metabisulfite, 39 mg of sodium metabisulfite, 76 mg of sodium sulfide nonahydrate and 563 mg of inert ingredients).

Treatment outcome: At the end of the second month, the tumor had disappeared Patient's status was diagnosed as normal with total remission.

Patient is still in good health 6 months after remission.

Utility Example 5

Patient: Male, 15 year-old

Baseline condition: Testis carcinoma with bone (spine) metastasis. Patient's status diagnosed as terminal.

Treatment regime: Administration of 18 capsules per day, each containing 1000 mg of a formulation prepared as in "formulation example 4" (approximately 280 mg of sodium thiosulfate, 42 mg of potassium metabisulfite, 39 mg of sodium metabisulfite, 76 mg of sodium sulfide nonahydrate and 563 mg of inert ingredients).

Treatment outcome: At the end of the second week all subjective symptoms (pain, chronic fatigue, etc.) had disappeared.

At the end of the sixth week the spine tumor had disappeared.

Patient decided (on his own) to discontinue treatment and did so during the seventh, eighth, and ninth weeks. At the end of the ninth week, alarming symptoms forced the patient to seek help again: a CAT-scan showed the presence of two new tumors (one on a different spine location and the other in the previously unaffected testis) and the treatment was reinstituted with marked abatement of subjective cancer symptoms. When patient was confronted with the need to surgically ablate the previously unaffected testis, he refused and again discontinued treatment. Patient died two weeks after discontinuing treatment.

Utility Example 6

Patient: Male, 4 year-old.

Baseline condition: Rhabdomyosarcoma of the nasopharynx, phase 4, refractory to radiotherapy and conventional chemotherapy. Patient's status diagnosed as terminal.

Treatment regime: 10 capsules per day, each containing 1000 mg of a formulation prepared as in "formulation example 4".

Treatment outcome: At the end of the second week a CAT-scan showed a halving in tumor size. At the end of the first month, a C.A.T.-scan showed a 75% decrease in tumor size. At the end of the second month, a C.A.T.-scan showed an 85% decrease in tumor size.

Patient is now asymptomatic.

Utility Example 7

Patient: Male, 68 year-old.

Baseline condition: Lung carcinoma (phase 4) with bone (clavicle) metastasis, refractory to conventional chemotherapy. Patient's status diagnosed as terminal, with a life expectancy of at best two weeks.

Treatment regime: 16 capsules per day, each containing 1000 mg of a formulation prepared as in "formulation example 4"

Treatment outcome: At the end of the $12^{th}$ week, a CAT-scan showed no tumor growth. Since then, the patient has been asymptomatic for 5 months.

Utility Example 8

Patient: Female, 44 year-old.

Baseline condition: Breast adenocarcinoma, metastasized to bone and lymph nodes with the patient refusing to submit to either surgery or conventional chemotherapy.

Treatment regime: 20 capsules per day, each containing 1000 mg of a formulation prepared as in "formulation example 4".

Treatment outcome: At the end of the second week, a CAT-scan showed a 50% reduction in tumor size. At the end of the first month, a CAT-scan showed a 90% reduction in tumor size. At the end of the second month, patient status was diagnosed as normal with complete cancer remission.

Utility Example 9

Patient: Female, 55 year-old

Baseline condition: Uterine corpus carcinoma, phase 4. Patient's status diagnosed as terminal.

Treatment regime: 40 capsules per day, each containing 1000 mg of a formulation prepared as in "formulation example 4".

Treatment outcome: At the end of the third month, patient status was diagnosed as normal with complete cancer remission.

Utility Example 10

Patient: Male, 75 year-old

Baseline condition: Prostatic adenocarcinoma.

Treatment regime: 20 capsules per day, each containing 1000 mg of a formulation prepared as in "formulation example 4".

Treatment outcome: At the end of the sixth week, patient status was diagnosed as normal with complete cancer remission.

Utility Example 11

Patient: Female, 26 year-old.

Baseline condition: Gluteal cancer, phase 4, refractory to radiotherapy and to conventional chemotherapy. Patient's status was diagnosed as terminal after five unsuccessful attempts at tumor removal by surgery. Patient complained of continuous excruciating pain, not amenable to treatment with analgesics.

Treatment regime: 18 capsules per day, each containing 1000 mg of a formulation prepared as in "formulation example 4".

Treatment outcome: At the end of the third day the excruciating pain subsided, leaving behind a sensation of discomfort. At the end of the first week, both the pain and the discomfort had disappeared completely. At the end of the 6 h week there was evidence of massive tumor necrosis and concomitant reduction in tumor size.

Utility Example 12

Patient: Female, 49 year-old.
Baseline condition: Leg liposarcoma, still present after several unsuccessful attempts at tumor removal by surgery.
Treatment regime: 20 capsules per day, each containing 1000 mg of a formulation prepared as in "formulation example 4".
Treatment outcome: At the end of the sixth month, patient status was diagnosed as normal with complete cancer remission.

Utility Example 13

Patient: Male, 42 year-old
Baseline condition: Adenocarcinoma of the pancreas, phase 4. Patient status diagnosed as terminal.
Treatment regime: 25 capsules per day, each containing 1000 mg of a formulation prepared as in "formulation example 4.
Treatment outcome: At the end of the second month, patient status was diagnosed as normal with complete cancer remission.

Utility Example 14

Patient: Female, 34 year-old
Baseline condition: Multiple myeloma.
Treatment regime: 18 capsules per day, each containing 1000 mg of a formulation prepared as in "formulation example 4".
Treatment outcome: At the end of the second month, complete remission was observed.

Utility Example 15

Patient: Male, 58 year-old
Baseline condition: Hypercholesterolemia (total serum cholesterol 900 mg/dL).
Treatment regime: Administration of 20 capsules per day, each containing 1000 mg of a mixture prepared as in "formulation example 4"
Treatment outcome: At the end of the sixth week total blood cholesterol level was 200 mg/dL

Utility Example 16

Patient: Male, 63 year-old
Baseline condition: Hypercholesterolemia (total serum cholesterol 700 mg/dL).
Treatment regime: Administration of 20 capsules per day, each containing 1000 mg of a mixture prepared as in "formulation example 4"
Treatment outcome: At the end of the sixth week, total blood cholesterol level was 248 mg/dL.

Utility Example 17

Patient: Male, 74 year-old
Baseline condition: Hypercholesterolemia (total serum cholesterol 490 mg/dL).
Treatment regime: Administration of 20 capsules per day, each containing 1000 mg of a mixture prepared as in "formulation example 4"
Treatment outcome: At the end of the sixth week, total blood cholesterol level was 215 mg/dL.

Utility Example 18

Patient: Male, 76 year-old
Baseline condition: Hypercholesterolemia (total serum cholesterol 618 mg/dL).
Treatment regime: Administration of 20 capsules per day, each containing 1000 mg of a mixture prepared as in "formulation example 4"
Treatment outcome: At the end of the sixth week, total blood cholesterol level was 195 mg/dL.

Utility Example 19

Patient: Female, 56 year-old
Baseline condition: Hypercholesterolemia (total serum cholesterol 514 mg/dL).
Treatment regime: Administration of 20 capsules per day, each containing 1000 mg of a mixture prepared as in "formulation example 4"
Treatment outcome: At the end of the sixth week, total blood cholesterol level was 202 mg/dL.

Utility Example 20

Patient: Male, 50 year-old
Baseline condition: Hypercholesterolemia (total serum cholesterol 883 mg/dL).
Treatment regime: Administration of 20 capsules per day, each containing 1000 mg of a mixture prepared as in "formulation example 4"
Treatment outcome: At the end of the sixth week, total blood cholesterol level was 206 mg/dL.

Utility Example 21

Patient: Female, 58 year-old
Baseline condition: Hypercholesterolemia (total serum cholesterol 300 mg/dL).
Treatment regime: Administration of 20 capsules per day, each containing 1000 mg of a mixture prepared as in "formulation example 4"
Treatment outcome: At the end of the sixth week, total blood cholesterol level was 200 mg/dL.

Utility Example 22

Patient: Male, 63 year-old
Baseline condition: Hypercholesterolemia (total serum cholesterol 472 mg/dL).
Treatment regime: Administration of 20 capsules per day, each containing 1000 mg of a mixture prepared as in "formulation example 4"
Treatment outcome: At the end of the sixth week, total blood cholesterol level was 218 mg/dL.

Utility Example 23

Patient: Female, 3 year-old
Baseline condition: Down syndrome with severe mental retardation
Treatment regime: Administration of 10 capsules per day, each containing 1000 mg of a mixture prepared as in "formulation example 4"

Treatment outcome: At the end of the tenth day, cognitive ability had improved significantly as evidenced by an increased attention span, and development of verbal skills. Additionally there were improvements in sphincter control and muscle tone. At the end of the sixth month, cognitive development had reached a level similar to that of a normal 2 year old girl.

Utility Example 24

Patient: Female, 3 year-old
Baseline condition: Down syndrome with severe mental retardation and joint hyperflexibility.
Treatment regime: Administration of 10 capsules per day, each containing 1000 mg of a mixture prepared as in "formulation example 4" plus glucosamine sulfate (oral, 1500 milligrams per day), plus chondroitin sulfate (oral, 1200 milligrams per day).
Treatment outcome: At the end of the 14th day, cognitive ability had improved significantly as evidenced by an increased attention span and development of verbal skills. Additionally there were improvements in sphincter control and muscle tone. At the end of the sixth month, cognitive development had reached a level similar to that of a normal 2 year old girl. Additionally, a reduction in joint hyperflexibility was observed.

Utility Example 25

Patient: Female, 3 year-old
Baseline condition: Down syndrome with severe mental retardation
Treatment regime: Administration of 10 capsules per day, each containing 1000 mg of a mixture prepared as in "formulation example 4" plus coenzyme Q10 (oral, 300 milligrams per day).
Treatment outcome: At the end of the tenth day, cognitive ability had improved significantly as evidenced by an increased attention span and development of verbal skills. Additionally there were improvements in sphincter control and muscle tone. At the end of the fifth month, cognitive development had reached a level similar to that of a normal two-and-a-half year old girl.

Utility Example 26

Patient: Female, 4 year-old
Baseline condition: Down syndrome with severe mental retardation
Treatment regime: Administration of 10 capsules per day, each containing 1000 mg of a mixture prepared as in "formulation example 4"
Treatment outcome: At the end of the 10th day, cognitive ability had improved significantly as evidenced by an increased attention span and development of verbal skills. Additionally there were improvements in sphincter control and muscle tone. At the end of the twelfth month, cognitive development had reached a level similar to that of a normal 4 year old girl.

Utility Example 27

Patient: Female, 4 year-old
Baseline condition: Down syndrome with severe mental retardation
Treatment regime: Administration of 10 capsules per day, each containing 1000 mg of a mixture prepared as in "formulation example 4" plus multivitamins
Treatment outcome: At the end of the $10^{th}$ day, cognitive ability had improved significantly as evidenced by an increased attention span and development of verbal skills. Additionally there were improvements in sphincter control and muscle tone. At the end of the tenth month, cognitive development had reached a level similar to that of a normal 4 year old girl.

Utility Example 28

Patient: Female, 4 year-old
Baseline condition: Down syndrome with severe mental retardation
Treatment regime: Administration of 10 capsules per day, each containing 1000 mg of a mixture prepared as in "formulation example 4" plus choline (oral, 1000 milligrams per day) plus piracetam (oral, 1000 milligrams per day) plus pramiracetam (oral, 600 milligrams per day) plus selegiline (oral, 1 milligram per day), plus vinpocetine (oral, 5 milligrams per day), plus hydergine (oral, 5 milligrams per day)
Treatment outcome: At the end of the 10th day, cognitive ability had improved significantly as evidenced by an increased attention span and development of verbal skills. Additionally there were improvements in sphincter control and muscle tone. At the end of the seventh month, cognitive development had reached a level similar to that of a normal 4 year old girl.

Utility Example 29

Patient: Female, 4 year-old
Baseline condition: Down syndrome with severe mental retardation and hypothyroidism.
Treatment regime: Administration of 10 capsules per day, each containing 1000 mg of a mixture prepared as in "formulation example 4" plus triiodothyronine (oral, 10 mcg per day)
Treatment outcome: At the end of the 10th day, cognitive ability had improved significantly as evidenced by an increased attention span and development of verbal skills. Additionally there were improvements in sphincter control and muscle tone. At the end of the eleventh month, cognitive development had reached a level similar to that of a normal 4 year old girl.

Utility Example 30

Patient: Female, 4 year-old
Baseline condition: Down syndrome with severe mental retardation
Treatment regime: Administration of 10 capsules per day, each containing 1000 mg of a mixture prepared as in "formulation example 4" plus triiodothyronine (oral, 10 mcg per day).
Treatment outcome: At the end of the 10th day, cognitive ability had improved significantly as evidenced by an increased attention span and development of verbal skills. Additionally there were improvements in sphincter control and muscle tone. At the end of the tenth month, cognitive development had reached a level similar to that of a normal 4 year old girl.

Utility Example 31

Patient: Female, 4 year-old

Baseline condition: Down syndrome with severe mental retardation

Treatment regime: Administration of 10 capsules per day, each containing 1000 mg of a mixture prepared as in "formulation example 4" plus coenzyme Q10 (oral, 300 milligrams per day) plus triiodothyronine (oral, 10 mcg per day) plus choline (oral, 1000 milligrams per day) plus piracetam (oral, 1000 milligrams per day) plus pramiracetam (oral, 600 milligrams per day) plus niar (oral, 1 milligrams per day) plus hydergine (oral, 5 milligrams per day) plus vinpocetine (oral, 5 milligrams per day)

Treatment outcome: At the end of the 10th day, cognitive ability had improved significantly as evidenced by an increased attention span and development of verbal skills. Additionally there were improvements in sphincter control and muscle tone. At the end of the fifth month, cognitive development had reached a level similar to that of a normal 4 year old girl.

Utility Example 32

Patient: Male, 68 year-old

Baseline condition: Patient confined to bed after several episodes of acute myocardial infarction. Patient status diagnosed as terminal.

Treatment regime: Administration of 20 capsules per day, each containing 1000 mg of a mixture prepared as in "formulation example 4" plus coenzyme Q10 (oral, 1000 milligrams per day)

Treatment outcome: At the end of the third month patient blood pressure was normal and he was able to walk and exercise moderately.

While the invention has been described in connection with specific embodiments thereof, it will be understood that it is capable of further modification and that this patent application is intended to cover any variations, uses or adaptations following, in general, the principles of the invention and including such departures from the present disclosure as come within the ordinary skill of the art to which the invention pertains, and as may be applied to the essential features hereinbefore set forth, within the spirit of the invention.

What is claimed is:

1. A method of treating a mammal suffering from cancer, hypercholesterolemia, cardiovascular disease or Down syndrome, comprising the step of administering a pharmaceutical composition, said composition comprising a therapeutically effective amount of i) more than one active sulfur compound, or ii) at least one active sulfur compound plus a pharmaceutically acceptable carrier,
and wherein said active sulfur compound is selected from the group consisting of hydrogen sulfide, sodium hydrogen sulfide, sodium sulfide, potassium sulfide, calcium sulfide, sodium hydrosulfide dihydrate, sodium sulfide nonahydrate, and ammonium sulfide.

2. The method of claim 1, wherein the composition further comprises another pharmacologically active agent.

3. The method of claim 2, wherein said another pharmacologically active agent is a vitamin, a micronutrient, coenzyme Q10, glucosamine, chondroitin sulfate, triiodothyronine, vinpocetine, pramiracetam, piracetam, hydergine, choline, selegiline, gallic acid, diallyl sulfide, an anti-cancer agent, an immunostimulant, an antibiotic, a hormone antagonist, an antiviral agent, an antihypertension agent, insulin or an anti-inflammatory agent.

4. The method of claim 1, wherein the composition is administered orally, rectally, or by enteroclysis.

5. The method of claim 4, wherein the composition is administered orally by means of one or more capsules, each of said capsules comprising a shell, the active sulfur compound, and a pharmaceutically acceptable carrier, wherein the active compound is intimately admixed with and absorbed or adsorbed onto the carrier.

6. The method of claim 5, wherein the carrier comprises microcrystalline cellulose and water.

7. The method of claim 5, wherein the carrier comprises powdered cellulose and water.

8. The method of claim 4, wherein the composition is administered orally by means of one or more capsules, each of said capsules comprising a shell, the active sulfur compound, and a pharmaceutically acceptable carrier, wherein an enteric coating is present on the shell or on granules comprising the active sulfur compound, which are themselves enclosed by the shell.

9. The method of claim 4, wherein the composition is administered orally by means of a delayed-release formulation, said formulation comprising the active sulfur compound, and a pharmaceutically acceptable carrier.

10. The method of claim 4, wherein the composition is administered orally in the form of tablets coated with an enteric coating, or enterically-coated granules containing the active sulfur compound, said granules being included within a tablet.

11. The method of claim 1, wherein the composition is administered to the mammal parenterally, intravascularly, intramuscularly, intrathecally or subcutaneously.

12. The method of claim 1, wherein the oral composition is administered to the mammal transdermally, transmucosally, or sublingually.

13. The method of claim 1, wherein the composition is administered to the mammal so as to produce contact of said compound with its site of action in the mammal's body.

14. The method of claim 1, wherein the active sulfur compound is intimately admixing with wet microcrystalline or wet powdered cellulose for oral administration.

15. A method of treating a mammal suffering from a cancer, hypercholesterolemia, cardiovascular disease or Down syndrome, comprising the step of administering a pharmaceutical composition to a subject in need thereof, said composition comprising a therapeutically effective amount of a single active sulfur compound
wherein the sulfur compund is selected from the group consisting of hydrogen sulfied, sodium hydrogen sulfide, sodium sulfied, potassium sulfide, calcium sulfied, sodium hydrosulfide dihydrate, sodium sulfide nonahydrate, and ammonium sulfide.

16. The method of claim 15, wherein the composition is administered orally, rectally, or by enteroclysis.

17. The method of claim 16, wherein the composition is administered orally by means of one or more capsules, each of said capsules comprising a shell and the active sulfur compound, wherein an enteric coating is present on the shell or on granules comprising the active sulfur compound, which are themselves enclosed by the shell.

18. The method of claim 16, wherein the composition is administered orally by means of a delayed-release formulation, said formulation comprising the active sulfur compound.

19. The method of claim 16, wherein the composition is administered orally in the form of tablets coated with an enteric coating, or enterically-coated granules containing the active sulfur compound, said granules being included within a tablet.

20. The method of claim 15, wherein the composition is administered to the mammal parenterally, intravascularly, intramuscularly, intrathecally or subcutaneously.

21. The method of claim 15, wherein the composition is administered to the mammal transdermally, transmucosally, or sublingually.

22. The method of claim 15, wherein the composition is administered to the mammal so as to produce contact of said compound with its site of action in the mammal's body.

23. A method for preparing pharmaceutically-acceptable oral dosage forms comprising at least one active sulfur compound and capable of releasing the active ingredient or ingredients in the gut of a mammal in need thereof, said method comprises the steps of i) intimately admixing the active ingredient or ingredients with wet microcrystalline or wet powdered cellulose , and ii) placing said mixture inside hard gelatin capsules.

24. A method of treating cancer, hypercholesterolemia, cardiovascular disease or Down syndrome, said method comprising providing to a subject in need thereof a therapeutically effective amount of an active sulfur compound selected from the group consisting of hydrogen sulfide, sodium hydrogen sulfide, sodium sulfide, potassium sulfide, calcium sulfide, sodium hydrosulfide dihydrate, sodium sulfide nonahydrate, and ammonium sulfide.

* * * * *

UNITED STATES PATENT AND TRADEMARK OFFICE
CERTIFICATE OF CORRECTION

PATENT NO. : 8,389,005 B2  
APPLICATION NO. : 12/405165  
DATED : March 5, 2013  
INVENTOR(S) : Gabriel Gojon-Romanillos Page 1 of 1

It is certified that error appears in the above-identified patent and that said Letters Patent is hereby corrected as shown below:

Title Page 2, under OTHER PUBLICATIONS, Column 2, line 54, in Gojon, Gabriel, replace "Rrelative" with --Relative--.

In the Specification

Column 11, Lines 64-65, replace "a patient (on non-human mammal)" with --a patient (or non-human mammal)--.

Column 12, Line 41, replace "mdr" with --MDR--.

Column 16, Line 67, replace "end of the 6 h" with --end of the $6^{th}$--.

Column 22, Line 49, replace "compund" with --compound--;

Line 50, replace "hydrogen sulfied" with --hydrogen sulfide--;

Line 51, replace "sodium sulfied, potassium sulfide, calcium sulfied," with --sodium sulfide, potassium sulfide, calcium sulfide,--.

Signed and Sealed this  
First Day of October, 2013

Teresa Stanek Rea  
*Deputy Director of the United States Patent and Trademark Office*